United States Patent [19]

du Chaffaut et al.

[11] 4,165,389

[45] Aug. 21, 1979

[54] FERMENTATION PROCESS FOR THE PRODUCTION OF A PROTEIN RICH ANIMAL FEEDSTUFF FROM LIQUID DAIRY BY-PRODUCTS

[75] Inventors: Jean A. du Chaffaut, Neuilly; Claude R. Magnoux; Patrick L. C. Oberto, both of Lavera, all of France

[73] Assignee: The British Petroleum Company Limited, Middlesex, England

[21] Appl. No.: 880,138

[22] Filed: Feb. 22, 1978

[30] Foreign Application Priority Data

Feb. 25, 1977 [GB] United Kingdom ............... 08070/77

[51] Int. Cl.$^2$ ............................................. A23C 23/00
[52] U.S. Cl. ......................................... 426/42; 426/60
[58] Field of Search ...................... 426/42, 43, 41, 34, 426/60, 62; 195/82, 114, 100

[56] References Cited

U.S. PATENT DOCUMENTS

| | | | |
|---|---|---|---|
| 3,252,802 | 5/1966 | Cunningham | 426/623 |
| 3,818,109 | 6/1974 | Bechtle | 426/41 |
| 4,055,666 | 10/1977 | Jeffreys et al. | 426/41 |

OTHER PUBLICATIONS

American Type Culture Collection Catalogue of Strains, Twelfth Edition, 1976, pp. 227, 331 and 376.
"Difco Manual of Culture Media", Difco Publishers, 9th Edition, 1954, p. 251.
Merk Index, 8th Edition, 1968, p. 730.

*Primary Examiner*—R. B. Penland
*Attorney, Agent, or Firm*—Morgan, Finnegan, Pine, Foley & Lee

[57] ABSTRACT

Fermentation process for the production of protein rich animal feedstuffs from liquid dairy by-products containing lactose and lactic acid in which a lactose and lactic acid utilizing strain of a yeast of the genus Kluyveromyces is cultivated in a broth comprising the by-product in the presence of added nicotinic acid.

18 Claims, No Drawings

FERMENTATION PROCESS FOR THE PRODUCTION OF A PROTEIN RICH ANIMAL FEEDSTUFF FROM LIQUID DAIRY BY-PRODUCTS

The present invention relates to a fermentation process for the production of protein rich animal feedstuffs from liquid dairy by-products which contain lactose and lactic acid and in particular from by-products of the manufacture of cheese.

Liquid dairy by-products which contain lactose and lactic acid are well known. Some examples of this type of by-product are acid or sweet whey, the ultra filtrate of acid or sweet whey or milk, partially or wholly deproteinised whey or milk and such products having a reduced lactose content. With the possible exception of sweet whey the by-product is regarded in the dairy industry as a waste product which presents problems in its disposal. Crude acid whey has been used as a pig or poultry feed. The quantity of by-products of this type produced by most factories usually substantially exceeds the demand for the products in the immediate vicinity of the factory. Furthermore the selling price is not sufficient to justify either the cost of transporting the products in the liquid state or the cost of drying. Acid whey contains an appreciable quantity of milk protein and ultra filtration processes have been developed for removing this protein for use in cheese manufacture. Similar processes have been developed for recovering the protein from milk. Because of the low nitrogen content and high ash to nitrogen ratio the ultra filtrates of whey and milk are not suitable for use as animal feedstuffs without a further modification e.g. by blending with nitrogenous material. In addition products of this type are often unsuitable for use as feedstuffs for young animals e.g. calves and piglets on account of their high lactic acid content.

Fermentation processes are known for enriching the protein content of these by-products to give products which are suitable for use as animal feedstuffs. These processes are not entirely satisfactory and the demand for a satisfactory process for the conversion of the by-products into useful products has been strengthened by the growing tendency for legislation relating to the disposal of liquid effluents.

An object of the present invention is to provide a process for converting liquid dairy by-products of the foregoing type which contain lactose and lactic acid and in particular acid or sweet whey or the ultra filtrate of acid or sweet whey or milk or deionised products thereof into protein rich animal feedstuffs.

Accordingly the present invention is a fermentation process for the production of a protein rich animal feedstuff from a liquid dairy by-product containing lactose and lactic acid which comprises cultivating a lactose and lactic acid utilising strain of a yeast of the genus Kluyveromyces in the presence of a gas containing free oxygen in a broth comprising a nitrogen source, the liquid dairy by-product and added nicotinic acid.

Preferably the minimum quantity of nicotinic acid added should be such that the quantity present in the broth is sufficient to permit complete utilisation by the process yeast of the lactose and lactic acid present.

Strains of Kluyveromyces which can utilise lactose or lactic acid are known and any known strain can be used in the present process. Some examples of species from which the strains can be selected are *Kluyveromyces fragilis, K. aestuarii, K. bulgaricus, K. circerisporus, K. lactis, K. marxiaus and K. wickerhamii*. Strains of the species *Kluyveromyces fragilis* are particularly suitable.

Surprisingly we have found that the utilisation by lactose and lactic acid utilising strains of the genus Kluyveromyces of the lactose and lactic acid present in liquid dairy by-products of the type previously mentioned in this specification e.g. acid or sweet whey, or the ultra filtrate of whey or milk or deionised products thereof can be facilitated by increasing the nicotinic acid content of the by-products.

The lactose content of whey or deionised whey can be in the range 50 to 90 percent by weight in relation to the total solid content and the lactic acid content can be in the range 5 to 12 percent by weight. The nicotinic acid content can be in the range 0.2 to 0.7 milligrams per liter. The lactose content of milk ultra filtrate or the deionised filtrate can be in the range 80 to 90 percent by weight in relation to the total solid content and the lactic acid content can be in the range 1 to 3 percent by weight. The nicotinic acid content can be in the range 0.1 to 0.8 milligrams per liter. We have found that the minimum quantity of nicotinic acid in the dairy by-products which is required by lactose and lactic acid utilising strains of Kluyveromyces to permit optimum utilisation of the lactose is about 10 micrograms per gram of lactose and for lactic acid the minimum quantity is about 5.0 micrograms per gram of lactic acid. There does not appear to be an upper limit for the quantity of nicotinic acid which can be present. However, for economic reasons it is desirable to add the least quantity which is required to enhance utilisation of the lactose and lactic acid present in the dairy by-product.

Any liquid dairy by-product containing lactose and lactic acid can be used in the present process. Dairy by-products of this type have been mentioned previously in this specification. Some examples are acid or sweet whey or the ultra filtrate of acid, or sweet whey or milk or deionised products thereof. It is desirable in the present process to use by-products having a low ash content. The ash content is a measure of the quantity of inorganic ions present in the product. Animal feeds containing substantial amounts of inorganic ions can be unsuitable for use in the diet of young animals such as calves. The ash content of whey can be in the range 8 to 13 percent by weight of the total dry solids and the ash content of milk ultra filtrate can be in the range 5 to 9 percent by weight of the total dry solids. The deionised dairy by-products are particularly suitable. The ash content of deionised whey and milk ultra filtrate can be in the range 4 to 8 percent by weight of the total solids content. The principal ions removed by deionisation are chloride, sulphate, sodium and potassium. Normally sufficient phosphorus and potassium ions are left in the deionised products to meet the nutritional requirement of the process yeast. Phosphorus and potassium are regarded as some of the more costly elements in the nutritional requirement of the yeast.

Operation of the process can be either batch or continuous and can be either aseptic or non-aseptic. Continuous non-aseptic operation is preferred for economic reasons. The nicotinic acid can be added to the dairy by-product fed to the broth or directly to the broth. The quantity of added nicotinic acid required for continuous operation is usually in the range 0.4 to 2.5, preferably in the range 0.8 to 1.8 and usually about 1.6 milligrams per liter of the by-product fed to the broth. Most suitably the quantity of nicotinic acid added should be such as to give in the broth a nicotinic acid content in the range 10 to 60 and preferably 20 to 42 micrograms per gram of lactose and 50 to 320 and preferably 100 to 230 micrograms per gram of lactic acid. In batch operation the quantity of added nicotinic acid is usually in the range 0.5 to 1.8 milligrams per liter of the by-product. Most suitably the quantity of nicotinic acid added should be such as to give in the broth initially a nicotinic acid content in the range 12 to 42 micrograms per gram of lactose and 64 to 230 micrograms per gram of lactic acid.

The term nicotinic acid when used in this specification includes salts of the acid. Most suitably the acid can be in the form of an aqueous solution which is added to the broth or dairy by-product fed to the broth.

The process can be carried out in any type of fermenter. Vat type fermenters are preferred, principally for economic reasons. Air lift, stirred air lift and stirred fermenters can be used. The fermenter can have a central draught tube to assist in the circulation of broth.

The broth temperature can have a value in the range 20° C. to 40° C. Most suitably the temperature can have a value in the range 30° C. to 38° C. and preferably in the range 32° C. to 35° C.

The broth pH can have a value in the range 2.5 to 7.0. Most suitably the value can be in the range 3.0 to 5.0 and preferably in the range 3.0 to 40.0. Where ammonium ions are used as the nitrogen source the pH of the broth can be controlled by adding a constant quantity of ammonium ions to the broth in an amount which is required to satisfy the nitrogen requirement of the yeast and adding an acid such as sulphuric acid in response to variations in the pH. Alternatively a constant quantity of acid can be added depending on the type of dairy by-product and the pH controlled by addition of the ammonium ions. Where operation is continuous the dilution rate can be in the range 0.1 to 0.5 volume/volume/hour and preferably in the range 0.15 to 0.3 volume/volume/hour and usually in the range 0.15 to 0.2 volume/volume/hour.

The aeration rate can be in the range 500 to 900 meters per hour superficial velocity. Operation is usually at atmospheric pressure but pressures up to 5.0 bars can be used.

Any compound containing nitrogen which can be utilised by the yeast as a nitrogen source can be used in the present process. Most suitably the nitrogen source can be present in the broth in the form of ammonium ions or urea. A convenient method of providing ammonium ions is as gaseous ammonia injected into the broth. Alternatively ammonium hydroxide can be fed to the broth to give ammonium ions.

The cultivated broth can have a microbial solids content in the range 10 to 100 grams per liter and more usually in the range 20 to 50 grams per liter. In order to obtain a marketable product the broth can be concentrated by removal of water preferably by evaporation to give a solids content in the range 20 to 40 percent by weight. Apparatus and techniques for removing water by evaporation from cultivated fermentation broth are known and are suitable for use in the present process. Alternatively the broth can be concentrated by centrifugation or by precipitation and decantation. The concentrate can be used as such as a liquid animal feed. Alternatively the concentrate can be dried, for example by a spray drying technique, to give a solid animal feed. The dried product can have a protein content in the range 40 to 55 percent by weight in relation to the total weight of the product, an ash content in the range 10 to 20 percent by weight and a lipid content in the range 3.0 to 5.0 percent by weight. The product can be used as a general animal feedstuff and in particular in view of the lowered lactic acid content it is suitable for use as a feedstuff for young animals.

The process of the present invention is illustrated further by the following Example.

EXAMPLE 4000 liters of an acid whey were added to an air lift fermenter having a working volume of 12 cubic meters. The whey had an ash content of 12 percent by weight of total dry solids, a lactose content of 65 percent by weight, a lactic acid content of 12 percent by weight and a nicotinic acid content of 10 milligrams per kilogram of the total dry solids. The fermenter was an open vat having a circular cross section, a height of 10 meters and a diameter of 1.3 meters. Aeration was by means of a sparger capable of an air flow rate of 1000 cubic meters per hour.

The whey was seeded with a culture of a lactose and lactic acid utilising strain of the yeast *Kluyveromyces fragilis* and continuous aerobic non-aseptic operation commenced. The nitrogen source for the yeast was in the form of ammonium ions which were provided by gaseous ammonia injected into the broth. The pH of the broth was controlled at about 3.0 by the addition of sulphuric acid in response to variations in the pH. The temperature was controlled at about 35° C. Aeration was at a rate of 750 meters per hour superficial velocity. The whey was fed to the fermenter to give a dilution rate of 0.3 volume/volume/hour. An aqueous solution of nicotinic acid having a concentration of 0.4 grams per liter was fed to the broth in the fermenter at a rate of 4.8 liters per hour. The total quantity of nicotinic acid added in relation to whey feed was 1.6 milligrams per liter. Steady state continuous operation was established at a cell density of 25 grams per liter. The quantity of nicotinic acid present in the broth was 54 micrograms per gram of lactose and 290 micrograms per gram of lactic acid.

An analysis of the cultivated broth recovered from the fermenter gave a lactose content of 1.0 grams per liter and a lactic acid content of 0.25 grams per liter.

The cultivated broth from the fermenter was concentrated by passing it to a three stage falling film evaporator to give a dry matter content of 280 grams per liter. The concentrate was then passed to a spray drier where it was dried to a powdered product having a protein content of 46 percent by weight, a lactic acid content of 0.5 percent by weight, a lactose content of 2.5 percent by weight, an ash content of 19 percent by weight, a polysaccharide content of 29 percent by weight and a lipid content of 3.0 percent by weight.

The product can be used as an animal feedstuff in the diet of pigs, poultry and young animals e.g. calves or piglets.

In an alternative method for preparing a solid product, the broth was heated to 75° C. in a plate heat exchanger and passed to a HVQX210 Alfa Laval centrifuge to separate an aqueous fraction having a dry matter content of 200 grams per liter from a less dense aqueous fraction having a dry matter content of 15 grams per liter. The dense fraction was then spray dried to give a solid product in the form of a powder having a protein content of 58 percent by weight, and an ash content of 8 percent by weight. The less dense fraction was concentrated by evaporation and then spray dried to give a solid powdered product having a protein content of 38 percent by weight and an ash content of 40 percent by weight.

The products were satisfactory as animal feedstuffs when used separately or when blended together in different proportions.

By way of a control an experimental fermentation was carried out under identical conditions to those described in the Example with the exception that the nicotinic acid addition was omitted. The cultivated broth under steady state conditions of operation had a cell density of 12 grams per liter. An analysis of the broth gave a lactose content of 10 grams per liter and a lactic acid content of 0.25 grams per liter.

We claim:

1. A fermentation process for the production of a protein rich animal feedstuff from a liquid dairy by-product containing lactose and lactic acid which comprises cultivating a lactose and lactic acid utilising strain of a yeast of the genus Kluyveromyces in the presence of a gas containing free oxygen in a broth comprising a nitrogen source, the liquid dairy by-product and added nicotinic acid in an amount to give in the broth a minimum of 10 micrograms per gram of lactose and a minimum of 5 micrograms per gram of lactic acid whereby the total quantity of nicotinic acid is present in the broth in a sufficient amount to permit substantial utilization by said yeast of the lactose and lactic acid present.

2. A process as claimed in claim 1 in which the nicotinic acid is added separately to the broth as an aqueous solution.

3. A process as claimed in claim 1 in which the fermentation is continuous.

4. A process as claimed in claim 3 in which the quantity of nicotinic acid added is in the range 0.4 to 2.5 milligrams per liter of the dairy by-product fed to the broth.

5. A process as claimed in claim 3 in which the quantity of nicotinic acid added is such as to give in the broth a nicotinic acid content in the range 10 to 60 micrograms per gram of lactose and 50 to 320 micrograms per gram of lactic acid.

6. A process as claimed in claim 3 in which the dairy by-product is fed to the broth to give a dilution rate in the range 0.10 to 0.5 volume/volume/hour.

7. A process as claimed in claim 1 in which the temperature of the broth is in the range 30° C. to 38° C.

8. A process as claimed in claim 1 in which the pH is in the range 3.0 to 5.0

9. A process as claimed in claim 1 in which the nitrogen source is in the form of ammonium ions.

10. A process as claimed in claim 9 in which the ammonium ions are provided by gaseous ammonia injected into the broth.

11. A process as claimed in claim 1 in which the nitrogen source is urea.

12. A process as claimed in claim 1 in which the gas containing free oxygen is air which is supplied to the broth at a rate in the range 500 to 900 meters per hour superficial velocity.

13. A process as claimed in claim 1 in which the yeast is a strain of *Kluyveromyces fragilis.*

14. A process as claimed in claim 1 in which the cultivated broth is concentrated by removal of water therefrom and thereafter dried.

15. A process as claimed in claim 14 in which the broth is concentrated by evaporation to remove water.

16. A process as claimed in claim 14 in which the broth is concentrated by centrifugation to remove water.

17. A process as claimed in claim 14 in which the broth is concentrated by precipitation and decantation.

18. A process as claimed in claim 14 in which the concentrated broth is dried by a spray drying technique.

* * * * *